(12) United States Patent
Esswein et al.

(10) Patent No.: US 6,197,759 B1
(45) Date of Patent: Mar. 6, 2001

(54) OSTEOBLAST-SPECIFIC MITOGENS AND DRUGS CONTAINING SUCH COMPOUNDS

(75) Inventors: Angelika Esswein, Büttelborn; Lothar Kling, Mannheim, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/508,714

(22) PCT Filed: Sep. 30, 1998

(86) PCT No.: PCT/EP98/06214

§ 371 Date: Apr. 11, 2000

§ 102(e) Date: Apr. 11, 2000

(87) PCT Pub. No.: WO99/17781

PCT Pub. Date: Apr. 15, 1999

(30) Foreign Application Priority Data

Oct. 2, 1997 (EP) ................................................ 97117124

(51) Int. Cl.$^7$ .................... A61K 31/661; A61P 19/10; A61P 19/00; C07F 9/09
(52) U.S. Cl. .................... 514/119; 514/120; 558/170; 558/179; 558/182
(58) Field of Search ...................... 514/119, 120

(56) References Cited

U.S. PATENT DOCUMENTS

| | | |
|---|---|---|
| 4,164,560 | 8/1979 | Folkman et al. . |
| 5,238,965 | * 8/1993 | Piazza et al. .................... 514/844 |
| 5,565,439 | * 10/1996 | Piazza et al. .................... 514/844 |

FOREIGN PATENT DOCUMENTS

| | | |
|---|---|---|
| 195 44 635 | 6/1997 | (DE) . |
| 524 023 | 1/1993 | (EP) . |
| 567 391 | 10/1993 | (EP) . |
| 616 814 | 9/1994 | (EP) . |
| 625 522 | 11/1994 | (EP) . |
| 151 315 | 2/1991 | (PL) . |
| WO 91/18558 | 12/1991 | (WO) . |
| WO 93/00050 | 1/1993 | (WO) . |
| WO 93/20859 | 10/1993 | (WO) . |
| WO 94/28004 | 12/1994 | (WO) . |

OTHER PUBLICATIONS

Moolenaar, Journal of Biological Chemistry, vol. 270, No. 22, pp. 12949–12952 (1995).
Tokumura et al., Arzneim. Forsch., vol. 35, No. 3, pp. 587–592 (1985).
Cao et al., Plant Physiol., vol. 94, pp. 1199–1206 (1990).
Siddiqui et al., Cell. Signal., vol. 8, No. 5, pp. 349–354 (1996).
Ichihara et al., Eur. J. Biochem., vol., 167, pp. 339–347 (1987).
Chemical Abstracts No. 185787w, vol. 115, p. 137 (1997).
Guterman et al., Collagen Rel. Res., vol. 8, pp. 419–431 (1988).
Moolenaar, Current Opinion Cell Biology, vol. 7, No. 2, pp. 203–210 (1995).
Wood et al., Chemistry and Physics of Lipids, vol. 18, pp. 316–333 (1977).
Slotboom et al., Chemistry and Physics of Lipids, vol. 1, pp. 317–336 (1967).
Tokumura et al., J. Pharm. Pharmacol., vol. 43, pp. 744–778 (1991).
Hollinger, J. Biomed. Mater. Res., vol. 17, pp. 71–82 (1983).
Pfeilschifter et al., Endocrinology, vol. 126, No. 2, pp. 703–711 (1990).
Machie et al., Bone, vol. 11, pp. 295–300 (1990).
Stoffel et al., Hoppe–Seyler's Z. Physiol. Chem., vol. 347, pp. 94–101 (1966).
Kabashima, Chem. Ber., vol. 71, pp. 1073–1076 (1938).
Esswein, A. et al. Derwent World Patents Index, Abstract No. 97–350637 (1997).
Chemical Abstracts No. 108122p, vol. 67, p. 10177 (1967).
Chemical Abstracts, vol. 32, Cols. 5850–5851 (1938).

* cited by examiner

*Primary Examiner*—Michael G. Ambrose
(74) *Attorney, Agent, or Firm*—George W. Johnston; William H. Epstein; John P. Parise

(57) ABSTRACT

Osteoblast-specific mitogens and drugs containing such compounds can be used for treating metabolic bone diseases. These compounds include lysophosphatidylic acid derivatives selected from the group consisting of compounds of formula:

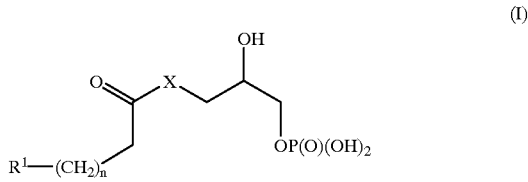

(I)

wherein $R^1$=alkenyl or alkynyl having from 6 to 24 carbon atoms;

n=0–12;

X=oxygen or NH;

the compounds (all-cis-5,8,11,14)-eicosatetraenoic acid 2-hydroxy-3-phosphonooxypropyl ester; cis-9, cis-12-octadecadienoic acid 2-hydroxy-3-phosphonooxypropyl ester; (all-cis-9,12,15)-octadecatrienoic acid 2-hydroxy-3-phosphonooxypropyl ester; cis-9-octadecenoic acid 2-hydroxy-3-phosphonooxypropyl ester; and erucic acid 2-hydroxy-3-phosphonooxypropylester being excluded, and the physiologically tolerable salts, esters, optically active forms, and racemates of said compounds, and derivatives of said compounds, salts, esters, optically active forms and racemates which can be metabolized in vivo to yield the corresponding compound of formula (I).

2 Claims, No Drawings

OSTEOBLAST-SPECIFIC MITOGENS AND DRUGS CONTAINING SUCH COMPOUNDS

The present invention relates to osteoblast-specific mitogenic compounds of formula (I), methods of preparing same, and drugs containing such compounds.

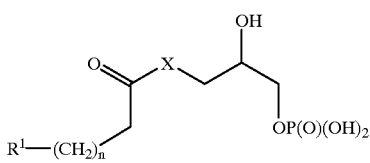

In healthy individuals, the formation and degradation processes in the bones are virtually at equilibrium, i.e., the activity of the osteoblasts and osteoclasts is balanced. However, if this equilibrium is disturbed in favor of the osteoclasts and/or to the disadvantage of the osteoblasts, a reduction in bone mass and a negative change in bone structure and function will be the result.

Up to now, bone resorption inhibitors such as estrogens, calcitonin and bisphosphonates are primarily used in the treatment of bone metabolic disorders. However, the use of these substances is limited and in addition, does not show the desired effect in all events. Compounds having a stimulating effect on bone formation and contributing to increase an already diminished bone mass are therefore of particular importance in the treatment of bone metabolic disorders. The European patent applications EP-A-625,522 and EP-A-524,023 describe substances having an osteoanabolic effect for osteoporosis therapy.

Lysophosphatidylic acid (LPA) is known to play a role as intracellular lipid messenger in various tissues and cell types (J. Biol. Chem. 270 (22), 12949–52, 1995; Curr. Opin. Cell. Biol. 7 (2), 203–10, 1995).

Surprisingly, it has now been found that the lysophosphatidylic acid derivatives of the present invention have a stimulating effect on bone formation and thus, are suitable for the general treatment of bone metabolic disorders. In particular, they can be used quite well in those cases where bone formation is disturbed, i.e., they are particularly suited for the treatment of osteopenic diseases of the skeletal system, such as osteoporosis, e.g., osteogenesis imperfecta, as well as for the local promotion of bone regeneration and osteoinduction, such as in orthopedic and orthodontic indications, in fracture curing, osteosyntheses, pseudarthroses and for bone implants to become incorporated.

Moreover, due to their influence on the bone metabolism, drugs containing the lysophosphatidylic acid derivatives of the present invention as active substances constitute a basis for the local and systemic treatment of rheumatoid arthritis, osteoarthritis and degenerative arthrosis.

The present invention is directed to new lysophosphatidylic acid derivatives of general formula (I)

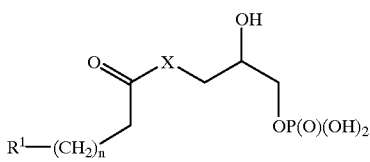

wherein $R^1$=alkyl, alkenyl or alkynyl having from 6 to 24 carbon atoms;

n=0–12;

X=oxygen or NH;

the compounds (all-cis-5,8,11,14)-eicosatetraenoic acid 2-hydroxy-3-phosphonooxypropyl ester, cis-9,cis-12-octadecadienoic acid 2-hydroxy-3-phosphonooxypropyl ester, (all-cis-9,12,15)-octadecatrienoic acid 2-hydroxy-3-phosphonooxypropyl ester, or cis-9-octadecenoic acid 2-hydroxy-3-phosphonooxy-propyl ester being excluded, and with the proviso that if X represents oxygen, n in the —$(CH_2)_n$—$CH_3$ group does not represent the numbers 7, 9, 11, 13, or 15, and to the physiologically tolerable salts, esters, optically active forms, racemates, and derivatives thereof which can be metabolized in vivo to yield compounds of general formula (I), and to the use of said compounds in the production of drugs.

Methods of synthesizing the above compound wherein X=oxygen, and —$(CH_2)_n$—$CH_3$ with n=13, are well-known (e.g., Chem. Ber. 71, 1075 (1938), Hoppe-Seyler's Z. Physiol. Chem. 347, 94–101 (1966)). Methods of synthesizing said compound wherein X=oxygen, and —$(CH_2)_n$—$CH_3$ with n=15, are well-known (e.g., Chem. Phys. Lipids 1, 317 (1966/67)). Methods of synthesizing said compound wherein X=oxygen, and —$(CH_2)_n$—$CH_3$ with n=7, are well-known (e.g., Chem. Phys. Lipids 18, 316 (1977)).

The compounds (all-cis-5,8,11,14)-eicosatetraenoic acid 2-hydroxy-3-phosphonooxypropyl ester, cis-9,cis-12-octadecadienoic acid 2-hydroxy-3-phosphonooxypropyl ester and (all-cis-9,12,15)-octadecatrienoic acid 2-hydroxy-3-phosphonooxypropyl ester are described to have an effect on the contraction of an isolated rat colon (J. Pharm. Pharmacol. 43, 774–78 (1991). An effect on blood pressure has been described for compounds wherein X=oxygen, and —$(CH_2)_n$—$CH_3$ with n=9, 11, 13, 15, as well as for cis-9-octadecenoic acid 2-hydroxy-3-phosphonooxypropyl ester, cis-9,cis-12-octadecadienoic acid 2-hydroxy-3-phosphonooxypropyl ester, and (all-cis-9,12,15)-octadecatrienoic acid 2-hydroxy-3-phosphonooxypropyl ester (Arzneim. Forsch. 35, 587–92 (1985)).

Each alkyl is understood to represent a straight-chain or branched $C_6$–$C_{18}$ alkyl group, such as hexyl, isohexyl, 2,2-dimethylhexyl, 5-methylhexyl, heptyl, isoheptyl, 6-methylheptyl, octyl, isooctyl, nonyl, isononyl, decyl, isodecyl, undecyl, isoundecyl, dodecyl, isododecyl, tridecyl, isotridecyl, tetradecyl, isotetradecyl, pentadecyl, isopentadecyl, hexadecyl, heptadecyl, isoheptadecyl, or octadecyl, particularly heptyl, decyl and dodecyl.

Each alkenyl represents an optionally substituted residue having 6–20 carbon atoms and one or more unsaturations, such as $\Delta^1$-hexenyl, $\Delta^1$-octenyl, $\Delta^9$-nonenyl, $\Delta^1$-decenyl, $\Delta^{10}$-decenyl, $\Delta^{1,4}$-decadienyl, $\Delta^{1,4,7}$-decatrienyl, $\Delta^{1,4,7,10}$-hexadecatetraenyl $\Delta^1$-dodecenyl, $\Delta^5$-dodecenyl, $\Delta^{1,4}$-undecadienyl, $\Delta^{14}$-tetradecenyl, particularly $\Delta^1$-decenyl, $\Delta^{1,4}$-decadienyl, $\Delta^{1,4,7}$-decatrienyl, wherein the double bonds may be cis or trans, and all combinations are possible in compounds having multiple unsaturations.

Each alkynyl represents an optionally substituted residue having 6–20 carbon atoms and one or more unsaturations, such as $\Delta^1$-decynyl, $\Delta^1$-nonynyl, $\Delta^{1,3}$-tetradecadiynyl, $\Delta^{1,3}$-hexadecadiynyl, $\Delta^{1,3}$-octadecadiynyl, particularly $\Delta^1$-decynyl.

Compounds wherein X represents NH are particularly preferred.

Examples of physiologically usable salts of the compound of formula (I) are salts with physiologically tolerable mineral acids such as hydrochloric acid, sulfuric acid, sulfurous acid or phosphoric acid, or with organic acids such as methanesulfonic acid, p-toluenesulfonic acid, acetic acid, trifluoroacetic acid, citric acid, fumaric acid, maleic acid, tartaric acid, succinic acid, or salicylic acid. Compounds of formula (I) having a free carboxyl group may also form salts with physiologically tolerable bases. Examples of these salts are alkali metal, alkaline earth metal, ammonium, and alkylammonium salts, such as sodium, potassium, calcium, or tetramethylammonium salts.

The compounds of general formula (I) contain at least one asymmetrical carbon atom and therefore, the present application is also directed to optically active compounds of general formula (I).

The pure enantiomers of the compounds of formula (I) wherein X=oxygen are obtained by using optically active alcohols which may be purchased or prepared according to well-known methods, e.g., by traditional racemate resolution via salt formation using optically active acids.

The pure enantiomers of the compounds of formula (I) wherein X=NH are obtained by using optically active aminoalcohols which may be purchased or prepared according to well-known methods, e.g., by traditional racemate resolution via salt formation using optically active acids, or by reduction of optically active amino acids.

The compounds of general formula (I) wherein X=oxygen are prepared according to per se known methods by removing the protective group $R_2$ from compounds of general formula (II)

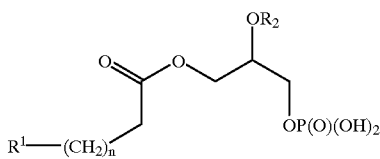

(II)

wherein $R_2$ represents a protective group commonly used for hydroxyl groups.

The compounds of general formula (II) are prepared according to per se known methods, preferably by reacting alcohols of general formula (III)

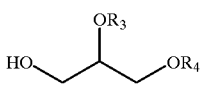

(III)

wherein $R_3$ and $R_4$ represent protective groups commonly used for hydroxyl groups, with protective groups for 1,2-diols, such as cyclic acetals and ketals being preferred, with carboxylic acid derivatives of general formula (IV)

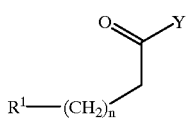

(IV)

wherein $R^1$ and n have the above-mentioned meanings and Y may be a hydroxy or an activating group, and if Y represents hydroxy, activation of the carboxyl group may be effected according to the carbodiimide method, and if Y represents an activating group, mixed anhydrides, particularly with carbonic acid lower alkyl esters such as ethyl or isobutyl esters, or active esters, particularly p-nitrophenyl, 2,4,5-trichlorophenyl, N-hydroxysuccinimide, or 1-hydroxybenzotriazol esters are possible to this end, to yield compounds of general formula (V)

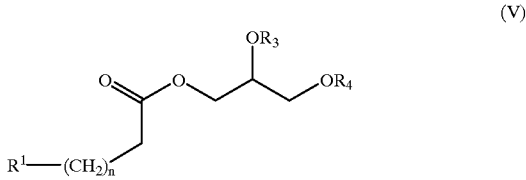

(V)

The compounds of general formula (III) are prepared according to per se known methods, preferably by introducing protective groups into glycerol, or may be purchased.

The compounds of general formula (IV) are prepared according to well-known methods starting from compounds of general formula (VI)

(VI)

wherein $R^1$ and n have the above-specified meanings.

The compounds of general formula (VI) are prepared according to well-known methods of chain extension or carboxylic acid synthesis, or may be purchased.

By removing the protective groups $R_3$ and $R_4$, the compounds of general formula (V) are converted to compound (VII)

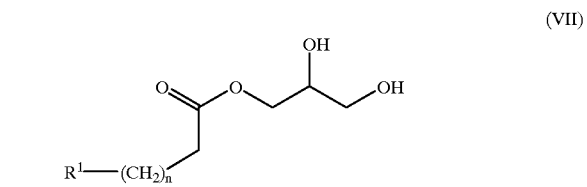

(VII)

In compounds of general formula (VII), the two hydroxyl groups are protected in orthogonal fashion by introducing common hydroxyl protecting groups $R_2$ and $R_6$, preferably by introducing a trityl group ($R_6$) at the primary hydroxyl function and a benzoate or silyl protective group such as tert-butyldiphenylsilyl ($R_2$) at the secondary hydroxyl group, to yield compounds of general formula (VIII)

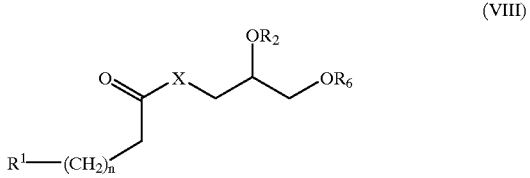

(VIII)

Initially, the compounds of general formula (VIII) are selectively deprotected according to per se known methods and then converted to compounds of general formula (II by reacting with phosphorus oxychloride.

The compounds of general formula (I) wherein X=NH are prepared according to per se known methods by removing the $R_2$ protective group from compounds of general formula (IX)

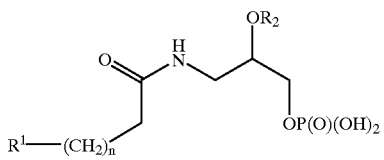

(IX)

wherein $R_2$ represents a protective group commonly used for hydroxyl groups.

The compounds of general formula (IX) are prepared according to per se known methods, preferably by reacting amines of general formula (X)

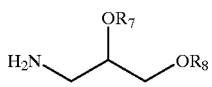

(X)

wherein $R_7$ and $R_8$ may independently represent hydrogen or a protective group commonly used for hydroxyl groups, with protective groups for 1,2-diols, such as cyclic acetals and ketals being preferred, with carboxylic acid derivatives of general formula (IV)

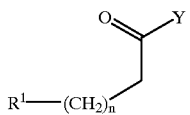

(IV)

wherein $R^1$, n and Y have the above-mentioned meanings, to yield compounds of general formula (XI)

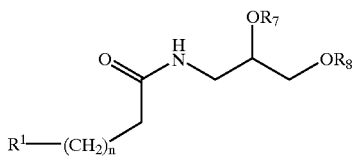

(XI)

In the event $R_7$ and $R_8$ represent hydrogen, the compounds of general formula (XI) are obtained in analogy to the method described above by using X=oxygen in the further reaction of compounds of general formula (VII).

In the event $R_7$ and $R_8$ are not orthogonal protective groups, the protective groups are removed initially according to common methods, and further proceeding is as in the case of $R_7$ and $R_8$=hydrogen.

If $R_7$ and $R_8$ are orthogonal protective groups, the primary hydroxyl group is selectively deprotected first and then reacted with phosphorus oxychloride to yield compounds of general formula (IX) wherein $R_2=R_7$.

Instead of using phosphorus oxychloride in the preparation of compounds of general formula (I), appropriately protected chlorophosphates of general formula (XII)

(XII)

wherein common protective groups, particularly methyl, ethyl or aryl are used for $R_9$ and $R_{10}$, may be reacted with compounds of general formula (XIII)

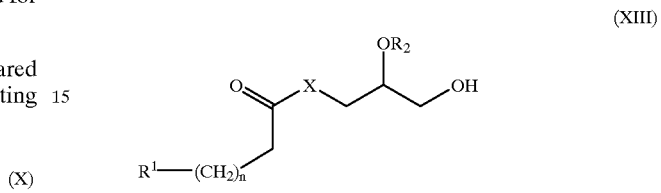

(XIII)

wherein $R_2$ represents a hydroxyl protecting group, preferably a benzoate or a silyl protective group. The compounds of general formula (XII) are commercially available or may be prepared according to methods well-known in literature (Houben-Weyl).

The compounds of general formula (I) are obtained by removing the protective groups $R_9$ and $R_{10}$ according to well-known methods.

As protective groups $R_2$, $R_3$, $R_4$, $R_5$, $R_6$, $R_7$, $R_8$, $R_9$, and $R_{10}$, in principle, all those well-known protective groups suitable for hydroxyl groups are possible as are described in Th. Greene, P. Wuts, "Protective Groups in Organic Synthesis", 2nd Edn., 1991, J. Wiley & Sons. Introduction and removal are effected according to common methods described therein.

The compounds of formula (I) may be administered in liquid or solid form or as aerosols on the oral, enteral, parenteral, topical, nasal, pulmonary or rectal routes in all the common non-toxic, pharmaceutically accepted carriers, adjuvants and additives. The compounds of formula (I) may also be applied locally on/in bones (optionally with surgical operation). The term "parenteral" includes subcutaneous, intravenous and intramuscular supply or infusions. Oral administration forms may be, e.g., tablets, capsules, coated tablets, syrups, solutions, suspensions, emulsions, elixirs, etc., which may contain one or more additives from the following groups, e.g., flavoring substances, sweeteners, colorants, and preservatives. Oral administration forms contain the active component together with non-toxic, pharmaceutically accepted carriers suitable for the production of tablets, capsules, coated tablets, etc., such as calcium carbonate, sodium carbonate, lactose, calcium phosphate or sodium phosphate; starch, mannitol, methylcellulose, talc, highly dispersed silicic acids, higher molecular weight fatty acids (such as stearic acid), peanut oil, olive oil, paraffin, Miglyol, gelatin, agar-agar, magnesium stearate, beeswax, cetyl alcohol, lecithin, glycerol, animal and vegetable fats, solid high molecular weight polymers (such as polyethylene glycols). Tablets, capsules, coated tablets, etc. may be provided with an appropriate coating such as glyceryl monostearate or glyceryl distearate, so as to prevent undesirable side effects in the stomach, or to result in prolonged activity due to delayed absorption in the gastrointestinal tract. Sterile injectable aqueous or oily solutions or suspensions are preferably used as injection media, which contain common additives such as stabilizers and solubilizers. Such additives may be, e.g., water, isotonic saline solution, 1,3-butanediol, fatty acids (such as oleic acid) mono- and diglycerides, or Miglyol. For rectal administration, all the suitable non-irritating additives may be used which are solid at normal temperatures and liquid at rectal temperature, such as cocoa butter and polyethylene glycol. For aerosol administration, the pharmaceutically common carrier media are used. For external application, creams, tinctures, gels, solutions or suspensions etc. with pharmaceutically common additives are used.

The dosage may depend on various factors such as the mode of application, species, age and/or individual condition. The doses to be administered daily or at intervals are around 1–1000 mg/person, preferably around 10–250 mg/person and may be ingested at one go or distributed over several times.

The compounds of formula (I) may be applied locally on/in bones (optionally with surgical operation). The application directly on/in bones (optionally with surgical operation) may be effected either in solution or suspension, conveniently by infusion or injection, locally or carrier-bound. For example, carrier-bound compounds of formula (I) may be applied as gels, pastes, solids or as coating on implants.

As carriers, biocompatible and preferably, biodegradable materials are used. Preferably, the materials themselves will additionally induce wound healing or osteogenesis.

For local application, it is preferred to embed the compounds of formula (I) in polymeric gels or films, thereby immobilizing them, and to apply these preparations directly on the area of the bone to be treated. These polymeric base gels or films consist of, e.g., glycerol, methylcellulose, hyaluronic acid, polyethylene oxides and/or polyoxamers. Collagen, gelatin and alginates are also suitable and are described in WO 93/00050 and WO 93/20859, for example. Other polymers are polylactic acid (PLA) and copolymers of lactic acid and glycolic acid (PLPG) (Hollinger et al., J. Biomed. Mater. Res. 17, 71–82 (1983)), and the "Demineralized Bone Matrix" (DBM) bone derivative (Guterman et al., Kollagen Rel. Res. 8, 419–4319 (1988)). Polymers such as those used for adsorbing TGFβ, for example, are also suitable and are described in EP-A 0,616,814 and EP-A 0,567,391, as well as the synthetic bone matrices according to WO 91/18558.

Materials commonly used when implanting bone substitutes or other therapeutically active substances are also suitable as carriers for the compounds of formula (I). Such carriers are also based on, e.g., calcium sulfate, tricalcium phosphate, hydroxyapatite and its biodegradable derivatives, and polyanhydrides. Apart from these biodegradable carriers, those carriers are also suitable which are not biodegradable, yet are biocompatible. For example, these carriers are sintered hydroxyapatite, bioglass, aluminates or other ceramic materials (e.g., calcium aluminate phosphate). These materials are preferably used in combination with said biodegradable materials, such as, in particular, polylactic acid, hydroxyapatite, collagen, or tricalcium phosphate. Other non-degradable polymers have been described in the U.S. Pat. No. 4,164,560, for example.

Particularly preferred is the use of carriers which continuously release the compounds of formula (I) at the site of action. Especially suited for this purpose are, e.g., the "slow release pellets" by Innovative Research of America, Toledo, Ohio, U.S.A. Particularly preferred is the use of pellets releasing the compounds of formula (I) over several days, preferably up to 100 days, at a daily dose of 1–10 mg/kg per day.

The dosage may depend on various factors such as the mode of application, species, age and/or individual condition. The doses of active substance to be administered daily are around from 0.01 mg to about 100 mg/kg body weight, preferably from 0.1 to 10 mg/kg body weight and may be applied at one go or distributed over several times.

Apart from the compounds mentioned in the examples, and the compounds which may be derived by combining all the meanings of the substituents mentioned in the claims, the following lysophosphatidylic acid derivatives, as well as their sodium and potassium salts are preferred in the meaning of the present invention:

Preferred Compounds (PC):

(1) Octanoic acid 2-hydroxy-3-phosphonooxypropyl ester
(2) 7-Methyloctanoic acid 2-hydroxy-3-phosphonooxypropyl ester
(3) 7,7-Dimethyloctanoic acid 2-hydroxy-3-phosphonooxypropyl ester
(4) Nonanoic acid 2-hydroxy-3-phosphonooxypropyl ester
(5) 4-Methylnonanoic acid 2-hydroxy-3-phosphonooxypropyl ester
(6) 8-Methylnonanoic acid 2-hydroxy-3-phosphonooxypropyl ester
(7) Undecanoic acid 2-hydroxy-3-phosphonooxypropyl ester
(8) 10-Methylundecanoic acid 2-hydroxy-3-phosphonooxypropyl ester
(9) 11-Methyldodecanoic acid 2-hydroxy-3-phosphonooxypropyl ester
(10) Tridecanoic acid 2-hydroxy-3-phosphonooxypropyl ester
(11) 12-Methyltridecanoic acid 2-hydroxy-3-phosphonooxypropyl ester
(12) 13-Methyltetradecanoic acid 2-hydroxy-3-phosphonooxypropyl ester
(13) Pentadecanoic acid 2-hydroxy-3-phosphonooxypropyl ester
(14) 14-Methylpentadecanoic acid 2-hydroxy-3-phosphonooxypropyl ester
(15) 15-Methylhexadecanoic acid 2-hydroxy-3-phosphonooxypropyl ester
(16) Heptadecanoic acid 2-hydroxy-3-phosphonooxypropyl ester
(17) 16-Methylheptadecanoic acid 2-hydroxy-3-phosphonooxypropyl ester
(18) 17-Methyloctadecanoic acid 2-hydroxy-3-phosphonooxypropyl ester
(19) Nonadecanoic acid 2-hydroxy-3-phosphonooxypropyl ester
(20) 18-Methylnonadecanoic acid 2-hydroxy-3-phosphonooxypropyl ester
(21) Eicosanoic acid 2-hydroxy-3-phosphonooxypropyl ester
(22) 19-Methyleicosanoic acid 2-hydroxy-3-phosphonooxypropyl ester
(23) 19-Methyl eicosanoic acid 2-hydroxy-3-phosphonooxy-propyl ester
(24) Heneicosanoic acid 2-hydroxy-3-phosphonooxypropyl ester
(25) Docosanoic acid 2-hydroxy-3-phosphonooxypropyl ester
(26) Tricosanoic acid 2-hydroxy-3-phosphonooxypropyl ester
(27) Tetracosanoic acid 2- hydroxy-3-phosphonooxypropyl ester
(28) Heptacosanoic acid 2-hydroxy-3-phosphonooxypropl ester

(29) Octacosanoic acid 2-hydroxy-3-phosphonooxypropyl ester
(30) Triacontanoic acid 2-hydroxy-3-phosphonooxypropyl ester
(31) 6-Heptenoic acid 2-hydroxy-3-phosphonooxypropyl ester
(32) trans-9-Hexadecenoic acid 2-hydroxy-3-phosphonooxypropyl ester
(33) (all-cis-11,14,17)-Eicosatrienoic acid 2-hydroxy-3-phosphonooxypropyl ester
(34) cis-10-Heptadecenoic acid 2-hydroxy-3-phosphonooxypropyl ester
(35) cis-10-Nonadecenoic acid 2-hydroxy-3-phosphonooxypropyl ester
(36) cis-3,cis-6-Nonadienoic acid 2-hydroxy-3-phosphonooxy propyl ester
(37) cis-10-Pentadecenoic acid 2-hydroxy-3-phosphonooxypropyl ester
(38) cis-12-Octadecenoic acid 2-hydroxy-3-phosphonooxypropyl ester
(39) cis-13-Octadecenoic acid 2-hydroxy-3-phosphonooxypropyl ester
(40) cis-7-Octadecenoic acid 2-hydroxy-3-phosphonooxypropyl ester
(41) cis-8-Eicosenoic acid 2-hydroxy-3-phosphonooxypropyl ester
(42) trans-9-Tetradecenoic acid 2-hydroxy-3-phosphonooxypropyl ester
(43) trans-9-Octadecenoic acid 2-hydroxy-3-phosphonooxypropyl ester
(44) (all-trans-9,11,13,15)-Octadecatetraenoic acid 2-hydroxy-3-phosphonooxypropylester
(45) (all-cis-9,11,13,15) Octadecatetraenoic acid 2-hydroxy-3-phosphonooxypropyl-ester
(46) cis-11-Octadecenoic acid 2-hydroxy-3-phosphonooxypropyl ester
(47) (all-cis-13,16,19)-Docosatrienoic acid 2-hydroxy-3-phosphonooxypropyl ester
(48) (all-cis-13,16,19)-Docosatrienoic acid 2-hydroxy-3-phosphonooxypropyl ester
(49) (all-cis-8,11,14)-Eicosatrienoic acid 2-hydroxy-3-phosphonooxypropyl ester
(50) trans-11-Octadecenoic acid 2-hydroxy-3-phosphonooxypropyl ester
(51) trans-13-Docosenoic acid 2-hydroxy-3-phosphonooxypropyl ester
(52) trans-9,trans-12-Octadecadienoic acid 2-hydroxy-3-phosphonooxypropyl ester
(53) cis-9-Tetradecenoic acid 2- hydroxy-3- phosphonooxypropyl ester
(54) cis-9-Hexadecenoic acid 2-hydroxy-3-phosphonooxypropyl ester
(55) 10-Undecenoic acid 2-hydroxy-3-phosphonooxypropyl ester
(56) cis-11,cis-14-Eicosadienoic acid 2-hydroxy-3-phosphonooxypropyl ester
(57) cis-11-Eicosenoic acid 2-hydroxy-3-phosphonooxypropyl ester
(58) cis-15-Tetracosenoic acid 2-hydroxy-3-phosphonooxypropyl ester
(59) 11-Dodecenoic acid 2-hydroxy-3-phosphonooxypropyl ester
(60) 9-Decenoic acid 2-hydroxy-3phosphonooxypropyl ester
(61) 16-Heptadecenoic acid 2-hydroxy-3-phosphonooxypropyl ester
(62) (all-cis-11,14,17)-Eicosatrienoic acid 2-hydroxy-3-phosphonooxypropyl ester
(63) cis-13-Eicosenoic acid 2-hydroxy-3-phosphonooxypropyl ester
(64) (all-cis-7,10,13,16)-Docosatetraenoic acid 2-hydroxy-3-phosphonooxypropylester
(65) 22-Tricosenoic acid 2-hydroxy-3-phosphonooxypropyl ester
(66) 9-Tetradecynoic acid 2-hydroxy-3phosphonooxypropyl ester
(67) 13-Eicosynoic acid 2-hydroxy-3-phosphonooxypropyl ester
(68) 10,12-Nonacosadiynoic acid 2-hydroxy-3-phosphonooxypropyl ester
(69) 10,12-Octadecadiynoic acid 2-hydroxy-3-phosphonooxypropyl ester
(70) 9-Octadecynoic acid 2-hydroxy-3-phosphonooxypropyl ester
(71) 10-Undecynoic acid 2-hydroxy-3-phosphonooxypropyl ester
(72) 10,12-Tricosadiynoic acid 2-hydroxy-3-phosphonooxypropyl ester
(73) 10,12-Pentacosadiynoic acid-2-hydroxy-3-phosphonooxypropyl ester
(74) 10,12-Heptacosadiynoic acid 2-hydroxy-3-phosphonooxypropyl ester
(75) Octanoic acid 2-hydroxy-3-phosphonooxypropylamide
(76) 7-Methyloctanoic acid 2-hydroxy-3-phosphonooxypropylamide
(77) 7,7-Dimethyloctanoic acid 2-hydroxy-3-phosphonooxypropylamide
(78) Nonanoic acid 2-hydroxy-3-phosphonooxypropylamide
(79) 4-Methylnonanoic acid 2-hydroxy-3-phosphonooxypropylamide
(80) 8-Methylnonanoic acid 2-hydroxy-3-phosphonooxypropylamide
(81) Decanoic acid 2-hydroxy-3-phosphonooxypropylamide
(82) Undecanoic acid 2-hydroxy-3-phosphonooxypropylamide
(83) 10-Methylundecanoic acid 2-hydroxy-3phosphonooxypropylamide
(84) Dodecanoic acid 2-hydroxy-3-phosphonooxypropylamide
(85) 11-Methyldodecanoic acid 2-hydroxy-3-phosphonooxypropylamide
(86) Tridecanoic acid 2-hydroxy-3-phosphonooxypropylamide
(87) 12-Methyltridecanoic acid 2-hydroxy-3-phosphonooxypropylamide
(88) Tetradecanoic acid 2-hydroxy-3-phosphonooxypropylamide
(89) 13-Methyltetradecanoic acid 2-hydroxy-3-phosphonooxypropylamide
(90) Pentadecanoic acid 2-hydroxy-3-phosphonooxypropylamide
(91) 14-Methylpentadecanoic acid 2-hydroxy-3-phosphonooxypropylamide
(92) Hexadecanoic acid 2-hydroxy-3-phosphonooxypropylamide
(93) 15-Methylhexadecanoic acid 2-hydroxy-3-phosphonooxypropylamide
(94) Heptadecanoic acid 2-hydroxy-3-phosphonooxypropylamide
(95) 16-Methylheptadecanoic acid 2-hydroxy-3-phosphonooxypropylamide
(96) Octadecanoic acid 2-hydroxy-3-phosphonooxypropylamide
(97) 17-Methyloctadecanoic acid 2-hydroxy-3-phosphonooxypropylamide

(98) Nonadecanoic acid 2-hydroxy-3-phosphonooxypropylamide
(99) 18-Methylnonadecanoic acid 2-hydroxy-3-phosphonooxypropylamide
(100) Eicosanoic acid 2-hydroxy-3-phosphonooxypropylamide
(101) 19-Methyleicosanoic acid 2-hydroxy-3-phosphonooxypropylamide
(102) 19-Methyleicosanoic acid 2-hydroxy-3-phosphonooxypropylamide
(103) Heneicosanoic acid 2-hydroxy-3-phosphonooxypropylamide
(104) Docosanoic acid 2-hydroxy-3-phosphonooxypropylamide
(105) Tricosanoic acid 2-hydroxy-3-phosphonooxypropylamide
(106) Tetracosanoic acid 2-hydroxy-3-phosphonooxypropylamide
(107) Heptacosanoic acid 2-hydroxy-3-phosphonooxypropylamide
(108) Octacosanoic acid 2-hydroxy-3-phosphonooxypropylamide
(109) Triacontanoic acid 2-hydroxy-3-phosphonooxypropylamide
(110) 6-Heptenoic acid 2-hydroxy-3-phosphonooxypropylamide
(111) trans-9-Hexadecenoic acid 2-hydroxy-3-phosphonooxypropylamide
(112) (all-cis-11,14,17)-Eicosatrienoic acid 2-hydroxy-3-phosphonooxypropylamide
(113) (all-cis-5,8,11,14)-Eicosatetraenoic acid 2-hydroxy-3-phosphonooxypropylamide
(114) cis-10-Heptadecenoic acid 2-hydroxy-3-phosphonooxypropylamide
(115) cis-10-Nonadecenoic acid 2-hydroxy-3-phosphonooxypropylamide
(116) cis-3,cis-6-Nonadienoic acid 2-hydroxy-3-phosphonooxypropylamide
(117) cis-10-Pentadecenoic acid 2-hydroxy-3-phosphonooxypropylamide
(118) cis-12-Octadecenoic acid 2-hydroxy-3-phosphonooxypropylamide
(119) cis-13-Octadecenoic acid 2-hydroxy-3-phosphonooxypropylamide
(120) cis-7-Octadecenoic acid 2-hydroxy-3-phosphonooxypropylamide
(121) cis-8-Eicosenoic acid 2-hydroxy-3-phosphonooxypropylamide
(122) trans-9-Tetradecenoic acid 2-hydroxy-3-phosphonooxypropylamide
(123) cis-9,cis-12-Octadecadienoic acid 2-hydroxy-3-phosphonooxypropylamide
(124) trans-9-Octadecenoic acid 2-hydroxy-3-phosphonooxypropylamide
(125) cis-9-Octadecnoic acid 2-hydroxy-3-phosphonooxypropyl amide
(126) (all-trans-9,11,13,15)-Octadecatetraenoic acid 2-hydroxy-3-phosphonooxypropylamide
(127) (all-cis-9,11,13,15)-Octadecatetraenoic acid 2-hydroxy-3-phosphonooxypropylamide
(128) cis-11-Octadecenoic acid 2-hydroxy-3-phosphonooxypropylamide
(129) (all-cis-13,16,19)-Docosatrienoic acid 2-hydroxy-3-phosphonooxypropylamide
(130) (all-cis-13,16,19)-Docosatrienoic acid 2-hydroxy-3-phosphonooxypropylamide
(131) (all-cis-9,12,15)-Octadecatrienoic acid 2-hydroxy-3-phosphonooxypropylamide
(132) (all-cis-8,11,14)-Eicosatrienoic acid 2-hydroxy-3-phosphonooxypropylamide
(133) trans-11-Octadecenoic acid 2-hydroxy-3-phosphonooxypropylamide
(134) trans-13-Docosenoic acid 2-hydroxy-3-phosphonooxypropylamide
(135) trans-9,trans-12-Octadecadienoic acid 2-hydroxy-3-phosphonooxypropylamide
(136) cis-9-Tetradecenoic acid 2-hydroxy-3-phosphonooxypropylamide
(137) cis-9-Hexadecenoic acid 2-hydroxy-3-phosphonooxypropylamide
(138) 10-Undecenoic acid 2-hydroxy-3-phosphonooxypropylamide
(139) cis-11,cis14-Eicosadienoic acid 2-hydroxy-3-phosphonooxypropylamide
(140) cis-11-Eicosenoic acid 2-hydroxy-3-phosphonooxypropylamide
(141) cis-15-Tetracosenoic acid 2-hydroxy-3-phosphonooxypropylamide
(142) 11-Dodecenoic acid 2-hydroxy-3-phosphonooxypropylamide
(143) 9-Decenoic acid 2-hydroxy-3-phosphonooxypropylamide
(144) 16-Heptadecenoic acid 2-hydroxy-3-phosphonooxypropylamide
(145) (all-cis-11,14,17)-Eicosatrienoic acid 2-hydroxy-3-phosphonooxypropylamide
(146) cis-13-Eicosenoic acid 2-hydroxy-3-phosphonooxypropylamide
(147) cis-13,cis-13-Docosadienoic acid 2-hydroxy-3-phosphonooxypropylamide
(148) (all-cis-7, 10,13,16)-Docosatetraenoic acid 2-hydroxy-3-phosphonooxypropylamide
(149) 22-Tricosenoic acid 2-hydroxy-3-phosphonooxypropylamide
(150) 9-Tetradecynoic acid 2-hydroxy-3-phosphonooxypropylamide
(151) 13-Eicosynoic acid 2-hydroxy-3-phosphonooxypropylamide
(152) 10,12-Nonacosadiynoic acid 2-hydroxy-3-phosphonooxypropylamide
(153) 10,12-Octadecadiynoic acid 2-hydroxy-3-phosphonooxypropylamide
(154) 9-Octadecynoic acid 2-hydroxy-3-phosphonooxypropylamide
(155) 10-Undecynoic acid 2-hydroxy-3-phosphonooxypropylamide
(156) 10,12-Tricosadiynoic acid 2-hydroxy-3-phosphonooxypropylamide
(157) 10,12-Pentacosadiynoic acid 2-hydroxy-3-phosphonooxypropylamide
(158) 10,12-Heptacosadiynoic acid 2-hydroxy-3-phosphonooxypropylamide Some process variants which may be used to synthesize the compounds according to the invention will be given in the following examples which, however, should not be construed as to be limiting to the subject of the invention. The structures of the compounds were established using $^1$H, $^{31}$P and optionally $^{13}$C-NMR spectroscopy. The purity of the substances was determined using C, H, N, P analysis and thin layer chromatography.

EXAMPLE 1 cis-9-Octadecenoic acid 2-hydroxy-3-phosphonooxypropyl ester cis-9-Octadecenoic acid 2,3-O-isopropylidenepropyl ester (1)

To a solution of 15.4 g (116 mmol) of 2,2-dimethyl-4-hydroxymethyldioxolane in 100 ml of pyridine is added dropwise 41.2 g (116 mmol) of 85% oleic acid chloride at room temperature. After 12 hours at room temperature the pyridine is removed, the residue is added with 2×50 ml of toluene and concentrated by evaporation. The residue is taken up in 200 ml of diethyl ether and extracted twice with 50 ml of 1N HCl and 50 ml of saturated NaCl solution. The ether phase is dried with $MgSO_4$, filtrated and concentrated. The residue is purified on a silica gel flash column using heptane/ethyl acetate (9:1). Yield: 26.3 g (61%).

cis-9-Octadecenoic acid 2,3-dihydroxypropyl ester (2)

24 g (60.5 mmol) 1 is dissolved in a mixture of THF/water (6:1) and cooled to 0° C. Then, trifluoroacetic acid (24 ml) is added dropwise, and the mixture is stirred for another 3 hours at 0° C. and warmed to room temperature. After 12 hours, cooling to 0° C. and neutralization with concentrated ammonia is effected. The THF is distilled off, and the residue is extracted with diethyl ether. The combined organic phases are dried over $MgSO_4$, filtrated and concentrated. The residue is purified on a silica gel column using heptane/ethyl acetate (1:1). Yield: 68% of a colorless oil.

cis-9-Octadecenoic acid 2-hydroxy-3-triphenylmethoxypropyl ester (3)

A solution of 2 (21 mmol) in 80 ml of dichloromethane/pyridine (1:1) is added dropwise with triphenylmethyl chloride (27 mmol) and stirred at room temperature for 48 hours. The solvent is removed, and the residue is added twice with 50 ml of toluene and concentrated. The residue is diluted with 100 ml of $H_2O$ and extracted three times with 50 ml of dichloromethane. The combined organic phases are washed with 50 ml of cold 5% HCl and 50 ml of saturated NaCl solution, dried over $MgSO_4$, filtrated and concentrated. The residue is purified by chromatography on silica gel using heptane/ethyl acetate (5:1). Yield: 88% of a colorless oil.

cis-9-Octadecenoic acid 2-tert-butyldiphenylsilyloxy-3-triphenylmethoxypropyl ester (4)

To a solution of 3 (5 mmol) in 30 ml of DMF is added imidazole (20 mmol) at 0° C. tert-Butyldiphenylsilyl chloride then is added dropwise to this mixture. The mixture is slowly warmed to room temperature. After 6 hours at room temperature, this is poured into ice water and extracted with ethyl acetate. The combined organic phases are washed with saturated NaCl solution, dried over $MgSO_4$, filtrated and concentrated. The residue is purified by silica gel chromatography using isohexane/ethyl acetate (9:1). Yield: 95% of a colorless oil.

cis-9-Octadecenoic acid 2-tert-butyldiphenylsilyloxy-3-hydroxypropyl ester (5)

4 ml of trifluoroacetic acid is slowly dropped into a solution of 4 (4.65 mmol) in 50 ml of dichloromethane at room temperature. After 3 hours, this is washed with water and saturated sodium hydrogen carbonate solution. The combined organic phases are dried over $MgSO_4$, filtrated and concentrated. The residue is purified on silica gel by flash chromatography using isohexane/ethyl acetate (7:1). Yield: 54% of a colorless oil.

cis-9-Octadecenoic acid 2-tert-butyldiphenylsilyloxy-3-phosphonooxypropyl ester (6)

A solution of phosphorus oxychloride (3 mmol) in 5 ml of tetrahydrofuran is cooled to 0° C. under nitrogen, and a solution of 5 (2.75 mmol) and pyridine (9.3 mmol) in 15 ml of tetrahydrofuran is added dropwise. The mixture is stirred at 0° C. for 30 minutes. Then, 3 ml of water is added, and stirring is effected for 20 hours at room temperature. This is subsequently acidified by dropwise addition of 1N HCl and extracted three times with 25 ml of ethyl acetate. The combined organic phases are dried over $MgSO_4$, filtrated and concentrated. The residue is subjected to chromatography on silica gel using ethyl acetate first and then methanol. Yield: 71% of a colorless oil.

cis-9-Octadecenoic acid 2-hydroxy-3-phosphonooxypropyl ester 6 (1 mmol) is dissolved in 10 ml of dichloromethane, and 25 ml of a 1% methanolic NaOH solution is added. This is concentrated after 20 hours at room temperature, and the residue is acidified with 1N HCl. The mixture is extracted with ethyl acetate. The combined organic phases are washed with 20 ml of $H_2O$ and dried over $MgSO_4$, filtrated and concentrated. The residue is treated with methanol. Yield: 78% of colorless crystals.

EXAMPLE 2 cis-9-Octadecenoic acid 2-hydroxy-3-phosphonooxypropylamide cis-9-Octadecenoic acid succinimide (8)

Dicyclcohexylcarbodiimide (24.1 g, 117 mmol) dissolved in THF is added to a solution of oleic acid (30 g, 106.2 mmol) in 150 ml of THF at 0° C. After 20 minutes, N-hydroxysuccinimide (13.5 g, 117 mmol) is added to the mixture. The mixture is slowly warmed to room temperature. After 18 hours at room temperature, cooling to 0° C. is effected, and the precipitate is sucked off. The filtrate is concentrated and purified on a silica gel column using ethyl acetate/heptene (1:3). Yield: 83% of a colorless wax.

cis-9-Octadecenoic acid 2,3-dihydroxypropylamide (9)

To a solution of cis-9-octadecenoic acid succinimide (18.3 g, 48.2 mmol) in 50 ml of acetonitrile is added 1-amino-2,3-propanediol (4.4 g, 48.2 mmol) in 50 ml of $H_2O$. After stirring for 12 hours at room temperature the acetonitrile is distilled off and the residue is extracted with ethyl acetate. The combined organic phases are extracted with saturated NaCl solution. The organic phase is dried with $MgSO_4$, filtrated and concentrated. The residue is crystallized from isohexane. Yield: 87% of a colorless powder.

cis-9-Octadecenoic acid 2-hydroxy-3-triphenylmethoxypropylamide (10)

A solution of 9 (28 mmol) in 80 ml of dichloromethane/pyridine (1:1) is added dropwise with triphenylmethyl chloride (36 mmol) and stirred at room temperature for 48 hours. The solvent is removed, and the residue is added twice with 50 ml of toluene and concentrated. The residue is diluted with 100 ml of $H_2O$ and extracted three times with 50 ml of dichloromethane. The combined organic phases are washed with 50 ml of cold 5% HCl and 50 ml of saturated NaCl solution, dried over $MgSO_4$, filtrated and concentrated. The residue is purified by chromatography on silica gel using heptane/ethyl acetate (2:1). Yield: 81% of a colorless oil.

cis-9-Octadecenoic acid 2-benzoyloxy-3-triphenylmethoxypropylamide (11)

Benzoyl chloride (30 mmol) is added dropwise at 0° C. to a solution of 10 (27.3 mmol) in 80 ml of dichloromethane/pyridine (1:1). Slow warming to room temperature is allowed to take place, and stirring is continued for another 4 hours at room temperature. The mixture is then concentrated, added twice with 50 ml of toluene and concentrated. The residue is added with 100 ml of $H_2O$ and extracted three times with 100 ml of dichloromethane. The combined organic phases are washed with 50 ml of cold 5% HCl and 50 ml of saturated NaCl solution, dried over $MgSO_4$, filtrated and concentrated. The residue is purified by silica gel chromatography using heptane/ethyl acetate (3:1). Yield: 87% of a colorless oil.

cis-9-Octadecenoic acid 2-benzoyloxy-3-phosphonooxypropyl-amide (12)

A solution of phosphorus oxychloride (7.1 mmol) in 10 ml (22 mmol) THF is added dropwise to a solution of 11 in 30 ml of tetrahydrofuran under nitrogen. The mixture is stirred at 0° C. for 30 minutes. Then, 5 ml of water is added, and stirring is effected for 20 hours at room temperature. The mixture is acidified by drop-wise addition of 1N HCl and extracted three times with 50 ml of ethyl acetate; the combined organic phases are dried over $MgSO_4$, filtrated and concentrated. The residue is subjected to chromatography on silica gel using ethyl acetate first and then methanol. Yield: 54% of a colorless oil.

cis-9-Octadecenoic acid 2-hydroxy-3-phosphonooxypropylamide (13)

12 (1.76 mmol) is dissolved in 20 ml of dichloromethane, and 50 ml of a 1% methanolic NaOH solution is added. This is concentrated after 20 hours at room temperature, and the residue is acidified with 1N HCl. The mixture is extracted with ethyl acetate. The combined organic phases are washed with 50 ml of $H_2O$ and dried over $MGSO_4$, filtrated and concentrated. The residue is treated with methanol. Yield: 82% of colorless crystals.

EXAMPLE 3

The compounds of formula (I) were examined in primary cultures of osteoblasts from fetal rat calvaria using a DNA synthesis assay. The experiments were performed following Pfeilschifter et al., Endocrinology 126, 703 (1990).
Test Specification: BrdU Method The DNA synthesis performance as a surrogate parameter for proliferation was determined using the cell proliferation ELISA, BrdU (colorimetric) by Boehringer Mannheim, Mannheim, Germany.

The primary osteoblasts were recovered by sequential digestion using collagenase from fetal rat calvaria, thus obtaining 5 cell fractions. A pool of cell fractions 3–5 was cultivated in vitro. The cells were cultivated in an incubator at a relative humidity of 95%, a $CO_2$ content of 5%, and a temperature of 37° C. The test substances were examined in cultures of the first, second or third cell passage.

For testing, the cells were seeded at a cell number of $7 \times 10^3$ cells (in 100 µl of culture medium)/well into flat-bottom micro-well plates (MWP) at least 96 hours prior to applying the test substances. To this end, MEM Dulbecco (plus 4.5 g/l of glucose, plus 3.7 g/l of $NaHCO_3$, with no glutamine) added with 5% fetal calf serum (FCS) and penicillin (100 U/ml)/streptomycin (0.1 mg/ml) was used as culture medium.

Immediately prior to adding the test substances to the cell culture, the medium was replaced by 100 µl of a medium containing 1 mg/ml bovine serum albumin (BSA) instead of FCS. The test substances were added at the desired concentrations to the BSA-containing medium. $TGF\beta_1$ (transforming growth factor $\beta_1$) at concentrations from 0.1 to 0.2 ng/ml was included as a positive control. Three determinations were carried out for each (positive) control and substance concentration, respectively.

Incubation of the cell cultures including test substances was effected over 24 hours, a BrdU probe (addition of 10 µl of a 100 µM 5-bromo-2'-deoxyuridine solution) additionally being present during the last 3 hours.

At the end of the incubation period, the cell lawn was fixed for 30 minutes using 200 µl of FixDenat™ solution at room temperature, simultaneously denaturing the DNA. The fixed cell lawn was subsequently covered with 100 µl of anti-BrdU-POD solution and incubated for 90 minutes at room temperature. After washing three times with 200 µl of PBS solution, the MWP wells were added with 100 µl of substrate solution (TMB=tetramethylbenzidine) and incubated for 5 minutes at room temperature.

The optical density was determined using an ATTC 340 MTP Reader by the SLT Company, where the wavelength of the measuring beam was 370 nm, and that of the reference beam was 492 nm. Recording and processing of the source data was performed using the "easyWINbasic" software by SLT Company.

Cell cultures which solely had received BSA-containing medium were used as controls (100%) in the assessment.

TABLE I

Effect of L-α-cis-9-octadecenoic acid 2-hydroxy-3-phosphonooxypropyl ester on the DNA synthesis rate of fetal rat osteoblasts

| Concentration (µg/ml) | 0.3 | 1.0 | 3.0 | 10.0 |
|---|---|---|---|---|
| Effect in % relative to control (control = 100%) | 161 ± 13 | 185 ± 12 | 253 ± 30 | 284 ± 22 |

Mean value ± standard deviation, n = 8

The compounds of formula (I) were also examined for stimulation of bone formation in an in vivo test model using Balb/c mice. The experiments were carried out following Mackie and Trechsel: Stimulation of bone formation in vivo by transforming growth factor-β: Remodeling of woven bone and lack of inhibition by indomethacin, Bone 11, 295–300, 1990.

TABLE II

Comparison of bone mass in controls and subsequent to local administration of L-α-cis-9-octadecenoic acid 2-hydroxy-3-phosphonooxypropyl ester to intact calottes of mice

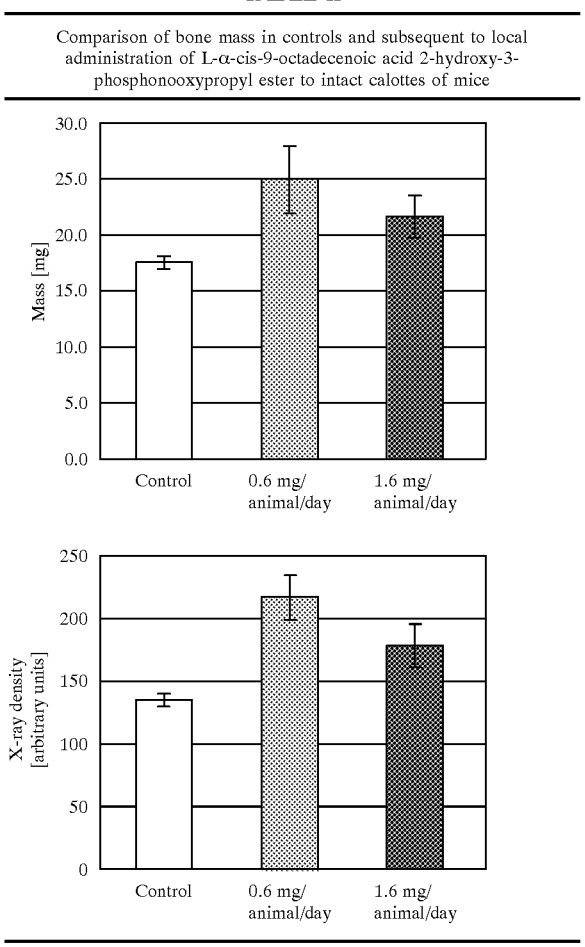

Mean value ± standard deviation, n = 6

TABLE III

Increase of bone mass in % relative to control, subsequent to local administration of L-α-cis-9-octadecenoic acid 2-hydroxy-3-phosphonooxypropyl ester to intact calottes of mice

|  | Mass | X-ray density |
| --- | --- | --- |
| 0.6 mg/animal/day | +37% | +58% |
| 1.6 mg/animal/day | +23% | +30% |

Mean value, n = 6

What is claimed is:

1. A method of treating a bone metabolic disorder in a patient comprising administering to the patient an effective amount of a lysophosphatidylic acid derivative selected from the group consisting of compounds of formula (I)

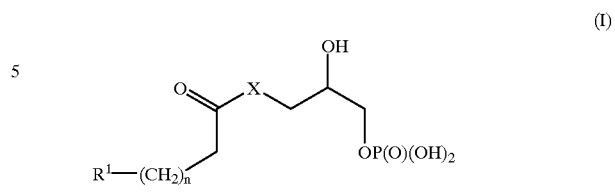

(I)

wherein $R^1$=alkyl, alkenyl or alkynyl having from 6 to 24 carbon atoms;

n=0–12;

X=oxygen or NH;

and the physiologically tolerable salts, esters, optically active forms, and racemates of said compounds, and derivatives of said compounds, salts, esters, optically active forms and racemates which can be metabolized in vivo to yield the corresponding compound of formula (I).

2. A method of treating a bone metabolic disorder in a patient, which comprises administering to the patient an effective amount of a lysophosphatidylic acid derivative selected from the group consisting of compounds of formula:

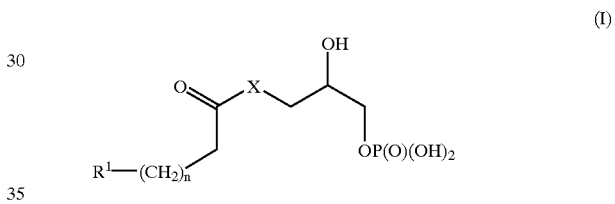

(I)

wherein $R^1$=alkenyl or alkynyl having from 6 to 24 carbon atoms;

n=0–12;

X=oxygen or NH;

the compounds (all-cis-5,8,11,14)-eicosatetraenoic acid 2-hydroxy-3-phosphonooxypropyl ester; cis-9, cis-12-octadecadienoic acid 2-hydroxy-3-phosphonooxypropyl ester; (all-cis-9,12,15)-octadecatrienoic acid 2-hydroxy-3-phosphonooxypropyl ester; cis-9-octadecenoic acid 2-hydroxy-3-phosphonooxypropyl ester; and erucic acid 2-hydroxy-3-phosphonooxypropylester being excluded, and the physiologically tolerable salts, esters, optically active forms, and racemates of said compounds, and derivatives of said compounds, salts, esters, optically active forms and racemates which can be metabolized in vivo to yield the corresponding compound of formula (I).

* * * * *